(12) United States Patent
Rodrigues et al.

(10) Patent No.: US 9,700,269 B2
(45) Date of Patent: Jul. 11, 2017

(54) PARALLEL TRANSVERSE FIELD (PTF) TILTED AND COLLIMATED DETECTORS

(71) Applicant: TOSHIBA MEDICAL SYSTEMS CORPORATION, Otawara (JP)

(72) Inventors: Miesher Lage Rodrigues, Buffalo Grove, IL (US); Hao Yang, Vernon Hills, IL (US); Liang Cai, Arlington Heights, IL (US); Gin Chung Wang, Lincolnshire, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 118 days.

(21) Appl. No.: 14/680,876

(22) Filed: Apr. 7, 2015

(65) Prior Publication Data

US 2016/0296184 A1 Oct. 13, 2016

(51) Int. Cl.
A61B 6/03 (2006.01)
A61B 6/00 (2006.01)

(52) U.S. Cl.
CPC ............ *A61B 6/4241* (2013.01); *A61B 6/032* (2013.01); *A61B 6/4291* (2013.01)

(58) Field of Classification Search
CPC .. A61B 6/03; A61B 6/032; A61B 6/42; A61B 6/4208; A61B 6/4241; A61B 6/4266; G01T 1/20; G01T 247/00
See application file for complete search history.

(56) References Cited

U.S. PATENT DOCUMENTS

| | | | |
|---|---|---|---|
| 7,187,750 B1* | 3/2007 | Hsieh | A61B 6/032 378/19 |
| 2010/0187429 A1* | 7/2010 | Engel | G01T 1/2928 250/370.09 |
| 2011/0211669 A1* | 9/2011 | Herrmann | G01T 1/249 378/19 |
| 2013/0251097 A1* | 9/2013 | Zou | A61B 6/032 378/9 |
| 2016/0081641 A1* | 3/2016 | Bouhnik | A61B 6/4435 378/5 |

* cited by examiner

*Primary Examiner* — David E Smith
(74) *Attorney, Agent, or Firm* — Oblon, McClelland, Maier & Neustadt, L.L.P.

(57) ABSTRACT

A computed tomography (CT) detector apparatus to increase energy resolution at a high count rate includes a plurality of fixed photon-counting detector (PCD) modules arranged in a ring, each PCD module including two Parallel-Transverse-Field (PTF) PCDs that are tilted with respect to a normal direction to a circumferential direction of the ring. Each PTF PCD includes a rectangular semiconductor crystal having a first face and a second face, wherein the first face and the second face are parallel, a cathode side including a cathode electrode covering the first face, and an anode side including a plurality of anode pixels on the second face. Each PTF PCD includes a collimator attached to a predetermined region of the PTF PCD, wherein the collimator blocks incident the X-rays.

12 Claims, 12 Drawing Sheets

US 9,700,269 B2

PARALLEL TRANSVERSE FIELD (PTF) TILTED AND COLLIMATED DETECTORS

FIELD

Embodiments disclosed herein generally relate to Parallel-Transverse-Field (PTF) tilted and collimated detectors to improve energy resolution at high count rates.

BACKGROUND

The X-ray beam in most computer tomography (CT) scanners is generally polychromatic. However, third-generation CT scanners generate images based upon data according to the energy integration nature of the detectors. These conventional detectors are called energy-integrating detectors and acquire energy-integrated X-ray data. On the other hand, photon-counting detectors are configured to acquire the spectral nature of the X-ray source, rather than the energy-integrated nature. To obtain the spectral nature of the transmitted X-ray data, the photon-counting detectors split the X-ray beam into its component energies or spectrum bins, and count a number of photons in each of the bins. The use of the spectral nature of the X-ray source in CT is often referred to as spectral CT. Since spectral CT involves the detection of the transmitted X-ray at two or more energy levels, spectral CT generally includes dual-energy CT by definition.

Photon-counting detectors in computed tomography imaging systems are often produced from semiconductor materials, such as Cadmium Zinc Telluride (CdZnTe), often referred to as CZT, Cadmium Telluride (CdTe), and Silicon (Si), among others. Traditional PTF direct-conversion photon-counting detectors (CdZnTe or CdTe) suffer from severe energy resolution loss in order to reduce charge time-of-flight. Further, pixelated non-PTF direct-conversion PCDs have long time-of-flight due to longer charge collection time, which limits the counting performance. Furthermore, polar effects and K-escape, which is caused by partial transport of the primary energy, e.g. X-ray energy, through another quantum, e.g. an X-ray quantum, to a neighboring pixel also degrade the performance in the detector.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

A hybrid-geometry photon-counting CT (PCCT) system was described in U.S. patent application Ser. No. 13/426,903, the contents of which are incorporated herein by reference. In the hybrid PCCT design, a ring of sparsely distributed photon-counting detectors is used to acquire spectral information in a fourth-generation CT geometry, while energy-integrating detectors acquire data using a third-generation geometry. The fourth-generation design can overcome challenges facing photon-counting detector technology, while the third-generation data can be used to maintain the spatial resolution and noise characteristics of the reconstruction.

In one embodiment, there is provided a computed tomography (CT) imaging apparatus, including a plurality of fixed photon-counting detector (PCD) modules arranged in a ring, each PCD module including a first Parallel-Transverse-Field (PTF) PCD that is tilted with respect to a normal direction to a circumferential direction of the ring and includes a collimator covering a predetermined region of the PTF PCD, wherein the collimator blocks incident X-rays.

In accordance with an exemplary embodiment, while a detector apparatus to improve energy resolution at high count rate is described and discussed below with reference to a computed tomography (CT) imaging system, it should be understood that the method and system of the invention may be applied to other imaging systems using photon-counting detectors.

Figure 1:
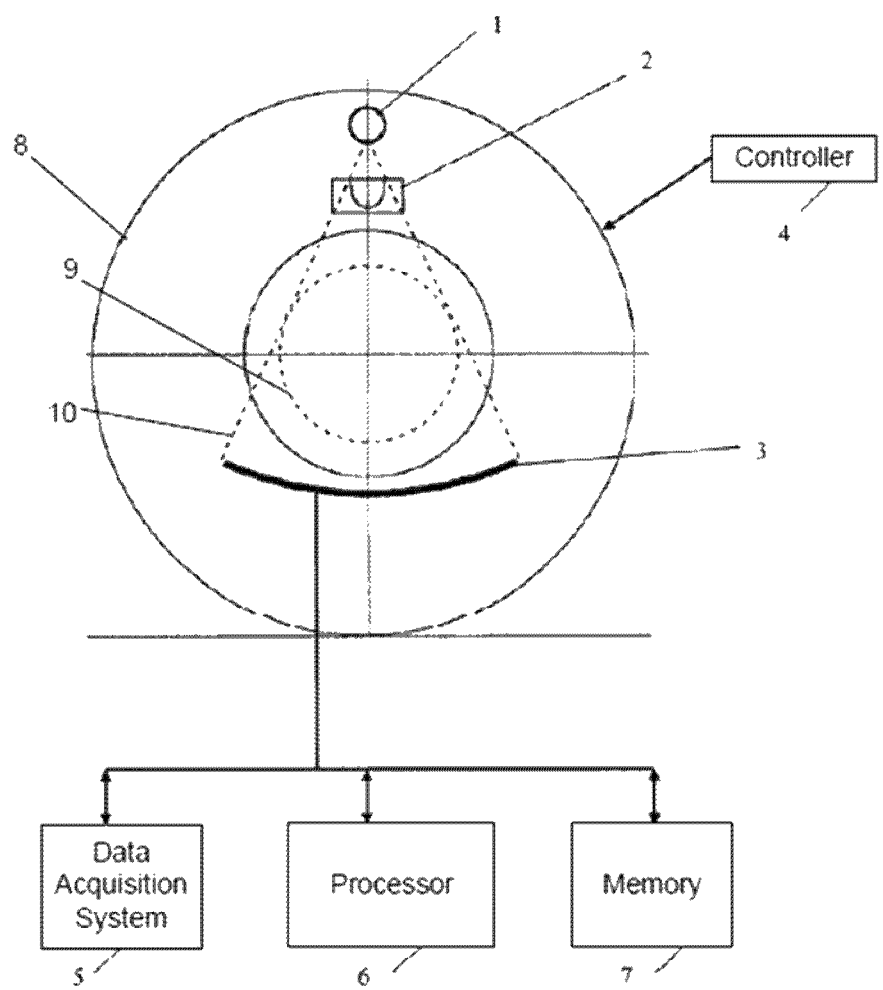
FIGS. 1 and 2 illustrate exemplary CT scanner systems.

FIG. 1 illustrates a simplified schematic structure of a CT apparatus that can include a detector array to detect photons. Aspects of this disclosure are not restricted to a CT apparatus as the medical imaging system. In particular, the structures and procedures described herein can be applied to other medical imaging systems, and the descriptions provided herein specifically relating to a CT apparatus and the detection of photons should be considered as exemplary. A detector array, a photon detector and/or a photon detector array may be referred to herein merely as a detector.

Figure 2:
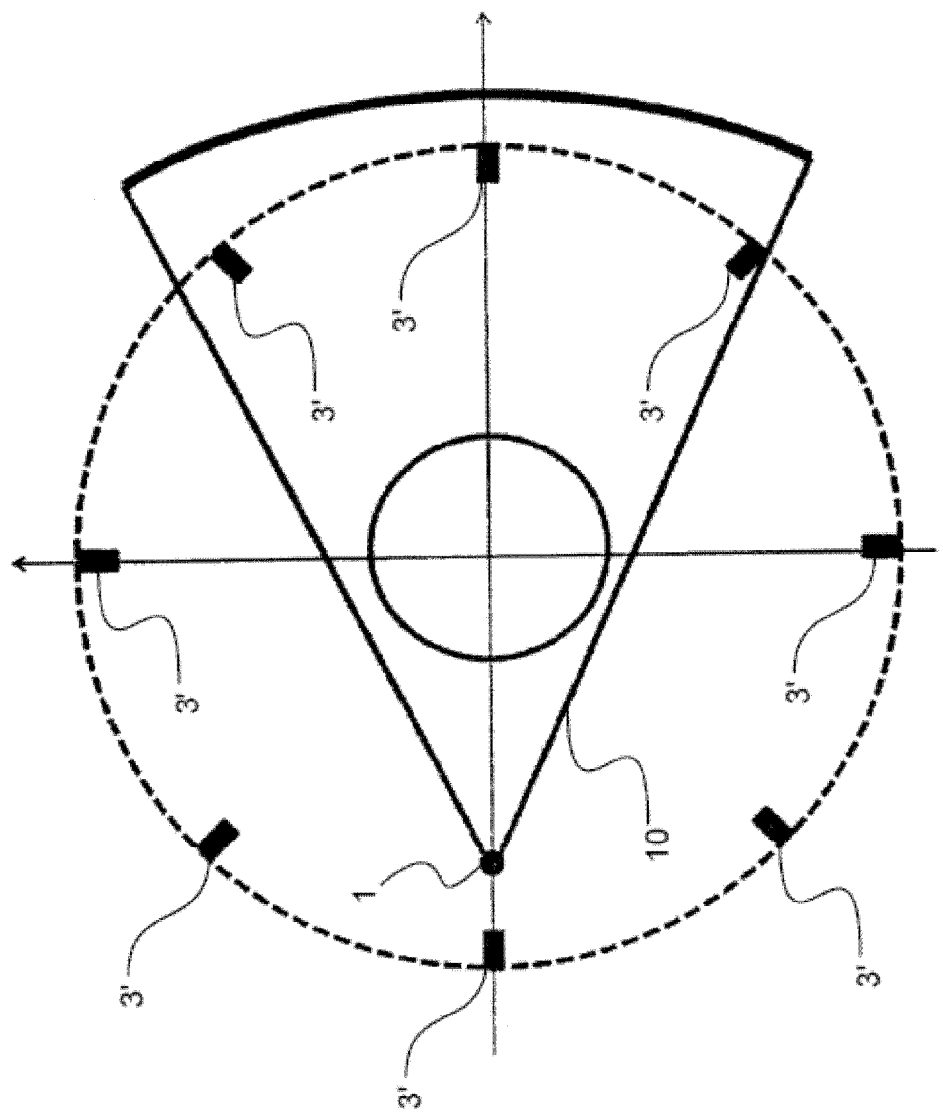

The CT apparatus illustrated in FIG. 1 includes an X-ray tube 1, filters and collimators 2, and a detector 3. The CT apparatus can also include sparse, fixed energy-discriminating (e.g., photon-counting) detectors 3', which can be arranged at a different radius from that of the third-generation detector, as shown in FIG. 2. The CT apparatus also includes additional mechanical and electrical components such as a gantry motor and a controller 4 to control the rotation of the gantry, control the X-ray source, and control a patient bed. The CT apparatus also includes a data acquisition system 5 and a processor 6. The processor 6 is configured to generate CT images based on the projection (view) data acquired by the data acquisition system. For example, the processor 6 includes a reconstruction processor to reconstruct spectral CT images. The processor is programmed to perform methods and execute algorithms in accordance with the processes, algorithms, equations and relationships described herein. The processor and data acquisition system can make use of a memory 7, which is configured to store, e.g., data obtained from the detector, detector pile-up models, and reconstructed images.

The X-ray tube 1, filters and collimators 2, detector 3, and controller 4 can be provided in a frame 8 that includes a bore. The frame 8 has a general cylindrical or donut shape. In the view shown in FIG. 1, a longitudinal axis of the bore of the frame 8 is in the center of the bore and extends into and out of the page. An interior of the bore, identified as area 9, is a target area for imaging. An object to be scanned, such as a patient, is placed in the target area with, e.g., a patient table. The object can then be irradiated by the X-ray tube 1 with a fan or cone of radiation 10, which generally, substantially or effectively cross-sects the object with respect to the longitudinal axis. The processor 6 is programmed to determine photon counts of captured incident X-ray photons. The data acquisition system 5, the processor 6, and the memory 7 can be implemented as a single machine or computer, or as separate machines or computers that are coupled together or distributed via a network or other data communication system. The controller 4 can also be coupled via the network or other data communication system, and can be implemented by a separate machine or computer, or as part of another machine or computer of the system.

In FIG. 1, the detector 3 is a rotational detector array that rotates with the X-ray tube 1 with respect to the longitudinal axis. A stationary detector array can also be included, thus providing a rotating detector array and a stationary array together in the frame 8. Other detector configurations can be implemented.

Figure 3:
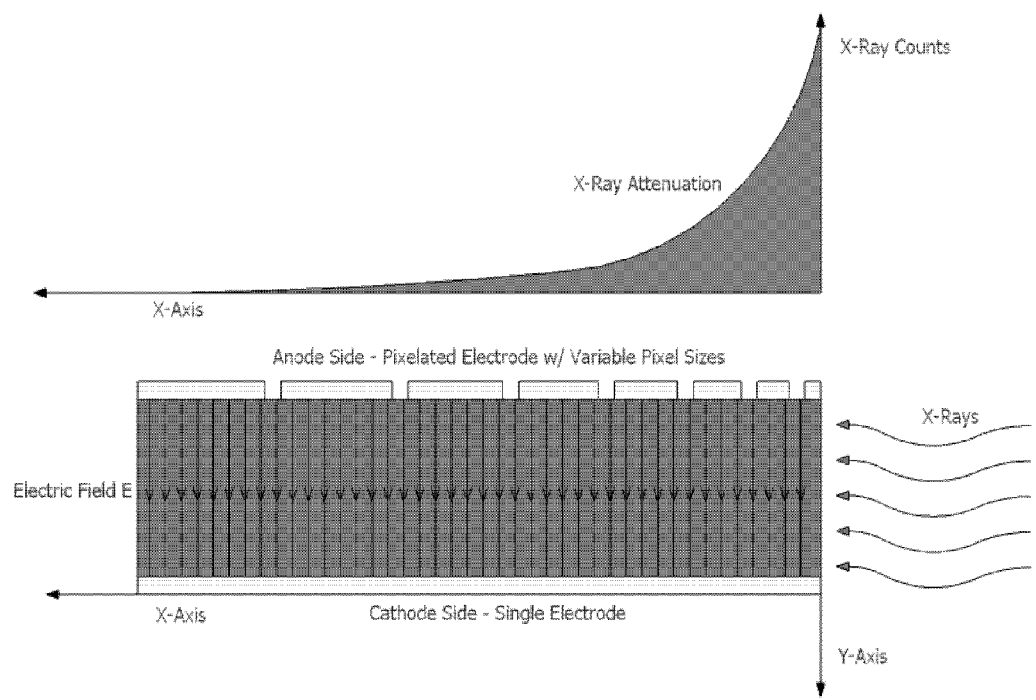
FIG. 3 illustrates an exemplary graph of X-ray attenuation inside a detector.

FIG. 3 illustrates a graph of X-ray attenuation inside a PTF photon-counting detector. In FIG. 3, the x-axis represents the depth of the detector, and the y-axis shows that the X-ray counts that are detected by the photon-counting detector (PCD). As illustrated in FIG. 3, the X-ray radiation intensity decreases in an exponential fashion with the depth of the detector, with the rate of decrease being controlled by the attenuation coefficient.

For a traditional PTF direct-conversion PCD, an anode-cathode distance can be of the order of 1 mm, while for PCDs with X-rays incident on the cathode, an anode-cathode distance of 2 to 3 mm is required. Therefore, the PTF direct-conversion PCDs show faster counting performance. Another advantage of PTF PCDs is that PTF PCDs can support higher count rates due to the multiple anode structures, where multiple small signals are eventually combined into a single large signal. However, traditional PTF direct-conversion photon-counting detectors (e.g., CdZnTe or CdTe) have disadvantages in providing spectral information due to position-dependent charge collection. Furthermore, pixelated non-PTF direct-conversion PCDs have a long time-of-flight due to a longer charge collection time than that of PTF direct-conversion PCDs, which limits the counting performance.

Figure 4:
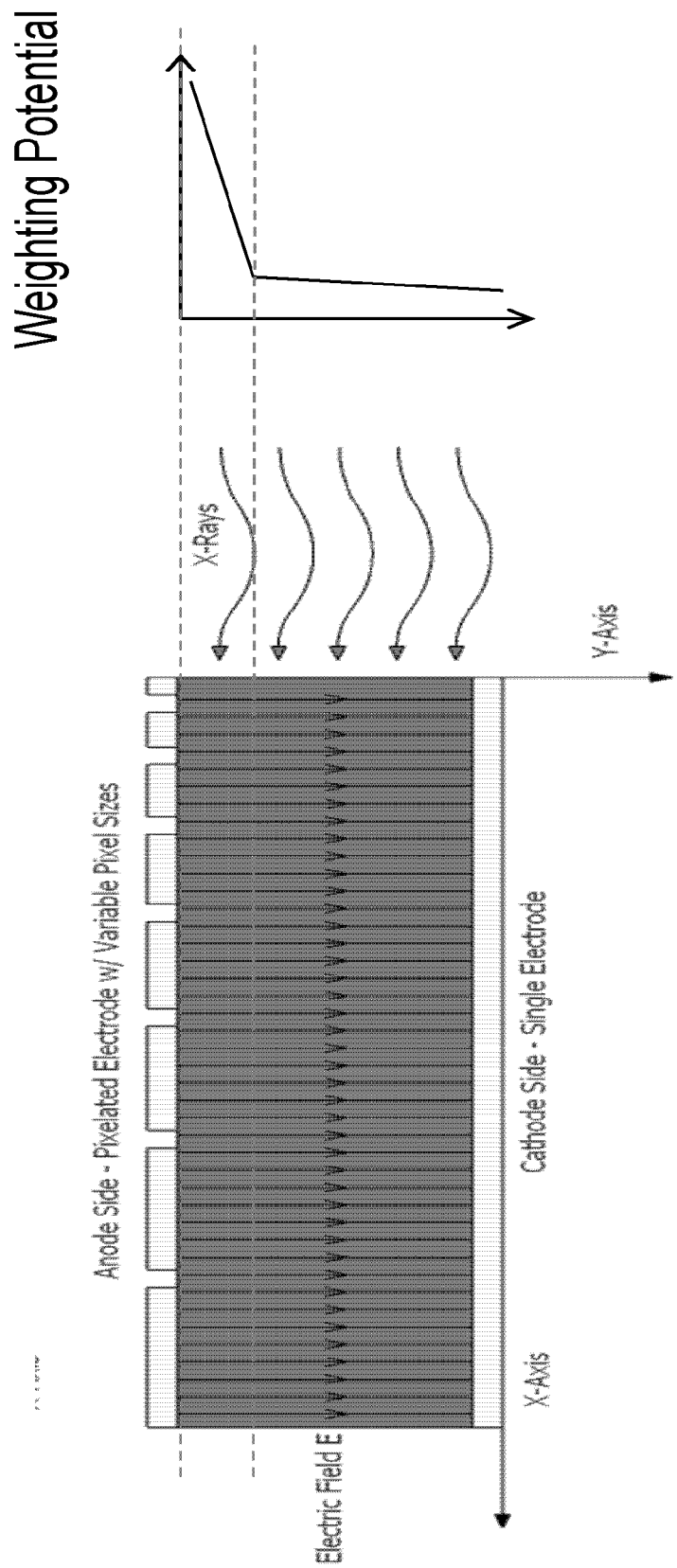
FIG. 4 illustrates an exemplary graph of a weighting potential of a conventional parallel-transverse field (PTF) direct conversion photon-counting detector.

For example, FIG. 4 shows a weighting potential for a pixelated PTF direct-conversion PCD relative to the depth of the detector. The weighting potential describes the coupling between the moving charges and the electrode of a charge when the moving charges drift in the detector. In the region between dotted lines, interactions provide very little energy information.

Figure 5:
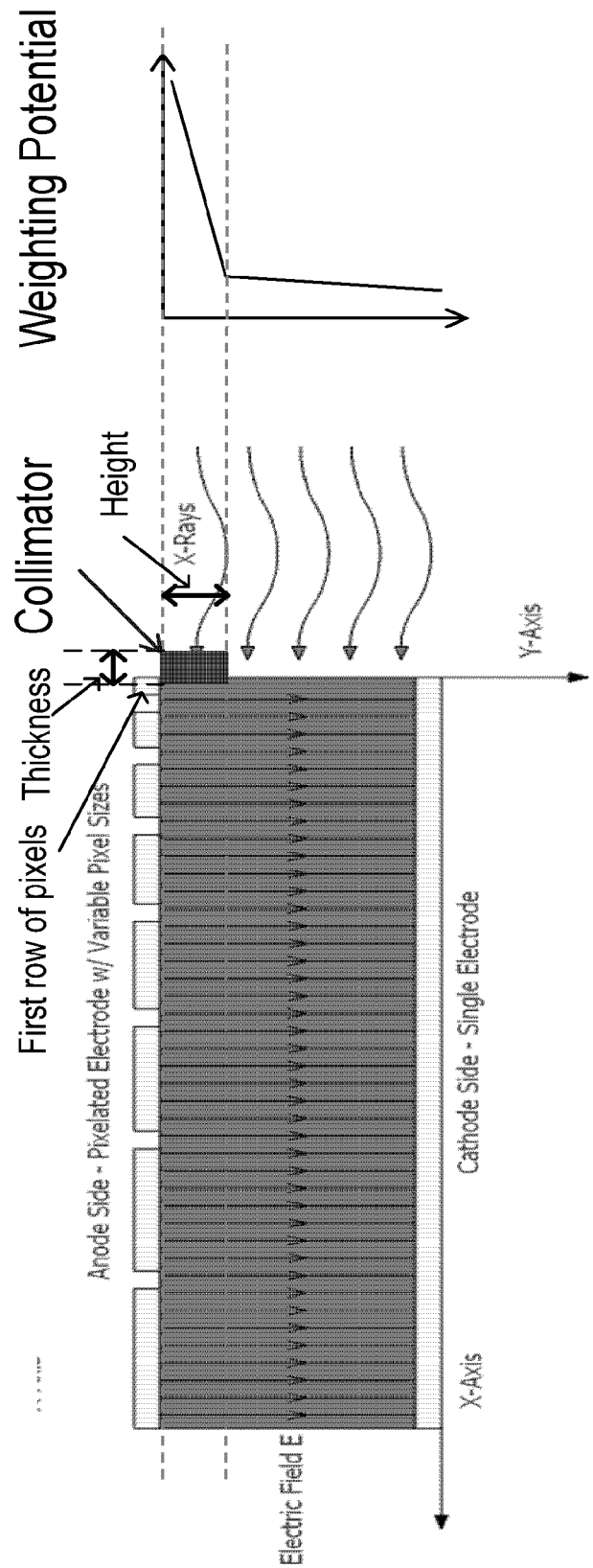
FIG. 5 illustrates an exemplary graph of a collimated PTF direct conversion photon-counting detector.

Now referring to FIG. 5, a first embodiment of the PTF direct-conversion PCD is illustrated. The first embodiment of the PTF direct-conversion PCD includes a pixelated PTF direct-conversion PCD and a collimator. The pixelated PTF direct-conversion PCD includes a crystal formed from a semiconductor material, such as CdZnTe or CdTe. A face of the crystal has a large single-cathode electrode. The opposite face of the crystal is the anode side, and includes an array of rectangular or square anode pixels with variable size. The collimator is attached to the crystal close to the anode side to block incident X-rays between the dotted lines (where the interactions between the incident X-rays and the detector has very little energy information). The collimator dimensions are functions of the electrode design (weighting potential) and can be optimized for differential application.

For example, the material and thickness of the collimator can be determined by the incident X-ray energies and the required photon-blockage efficiency. The height of the collimator is determined by a calculated weighting potential of the first row of pixels. FIG. 5 shows that the first row of pixels are the closest pixels to the entrance window of the X-ray photons in the PCD. The width of the collimator is determined based on the width of the detector.

Figure 6:
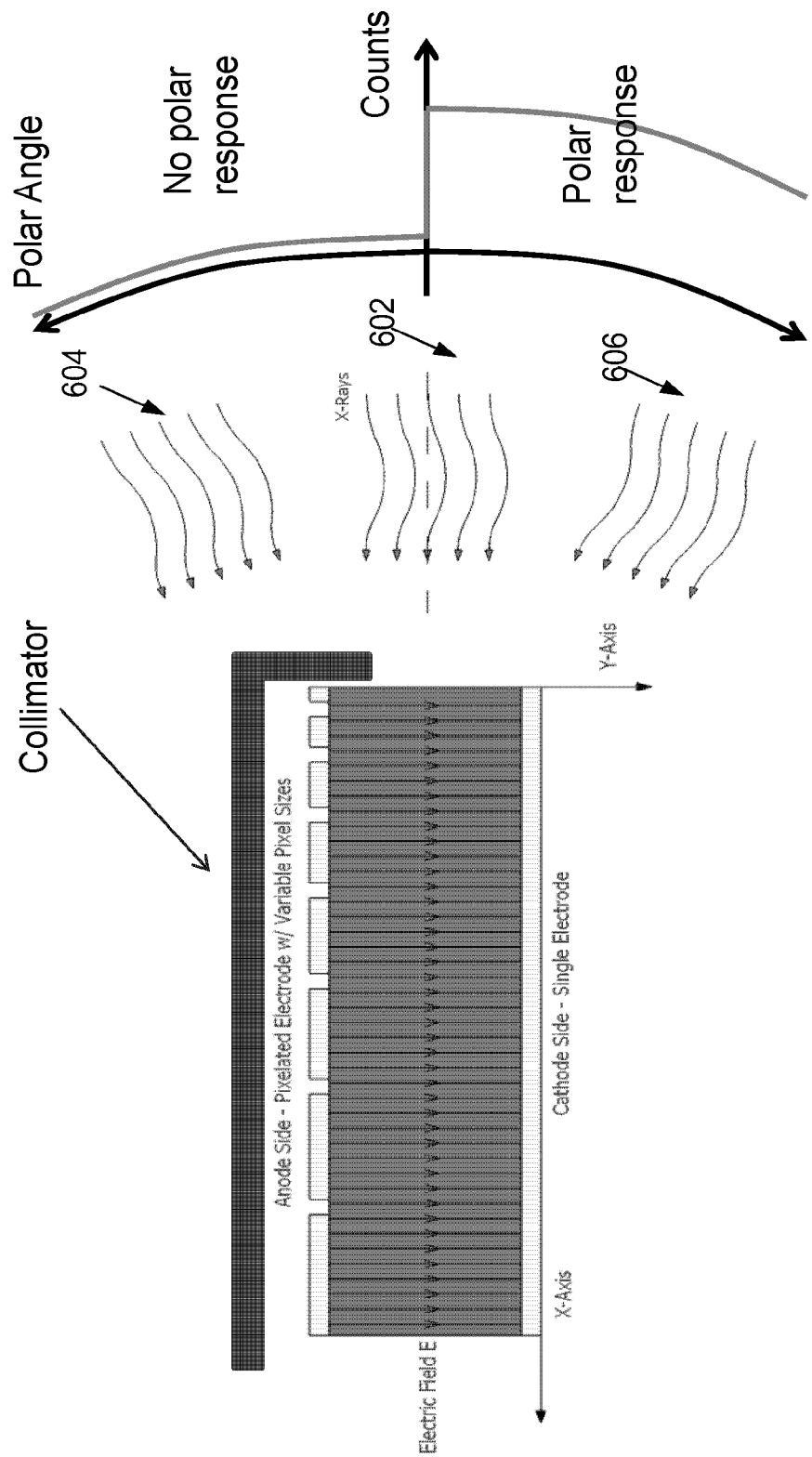
FIG. 6 illustrates an exemplary graph of a PTF direct conversion photon-counting detector with an extended collimated block.

Now referring to FIG. 6, a second embodiment of the PTF direct-conversion PCD is illustrated. This embodiment is implemented to reduce polar effects in a fourth-generation CT scanner. In the fourth-generation CT scanner, the detectors are on a stationary gantry, and the X-ray source rotates. Each detector receives X-rays from different incident angles as the source rotates. The detector response varies with the X-ray incident angle, which is referred to as the polar effect. The polar effect usually occurs for a non-normal entrance of incident photons, results in ambiguity in determining the response of the detector, and degrades overall spatial resolution in medical imaging systems. As shown in FIG. 6, when incident photons 604 and 606 are not perpendicular to the electrical field of the detector, the geometrical efficiency of the detector is different compared to the case for normal incidence rays 602. Thus, the polar effect needs to be integrated into the detector design for the sparse fourth-generation photon-counting detector geometry.

Thus, the second embodiment of the PTF direct-conversion PCD includes a pixelated PTF direct-conversion PCD and an extended collimator. The design of the PTF direct-conversion PCD is similar to the one described in FIG. 5. The extended collimator is used to block both the area where the interactions between the crystal and detector provide little energy information and the entire anode-side surface, to avoid X-rays incident at non-normal angles.

Figure 7A:
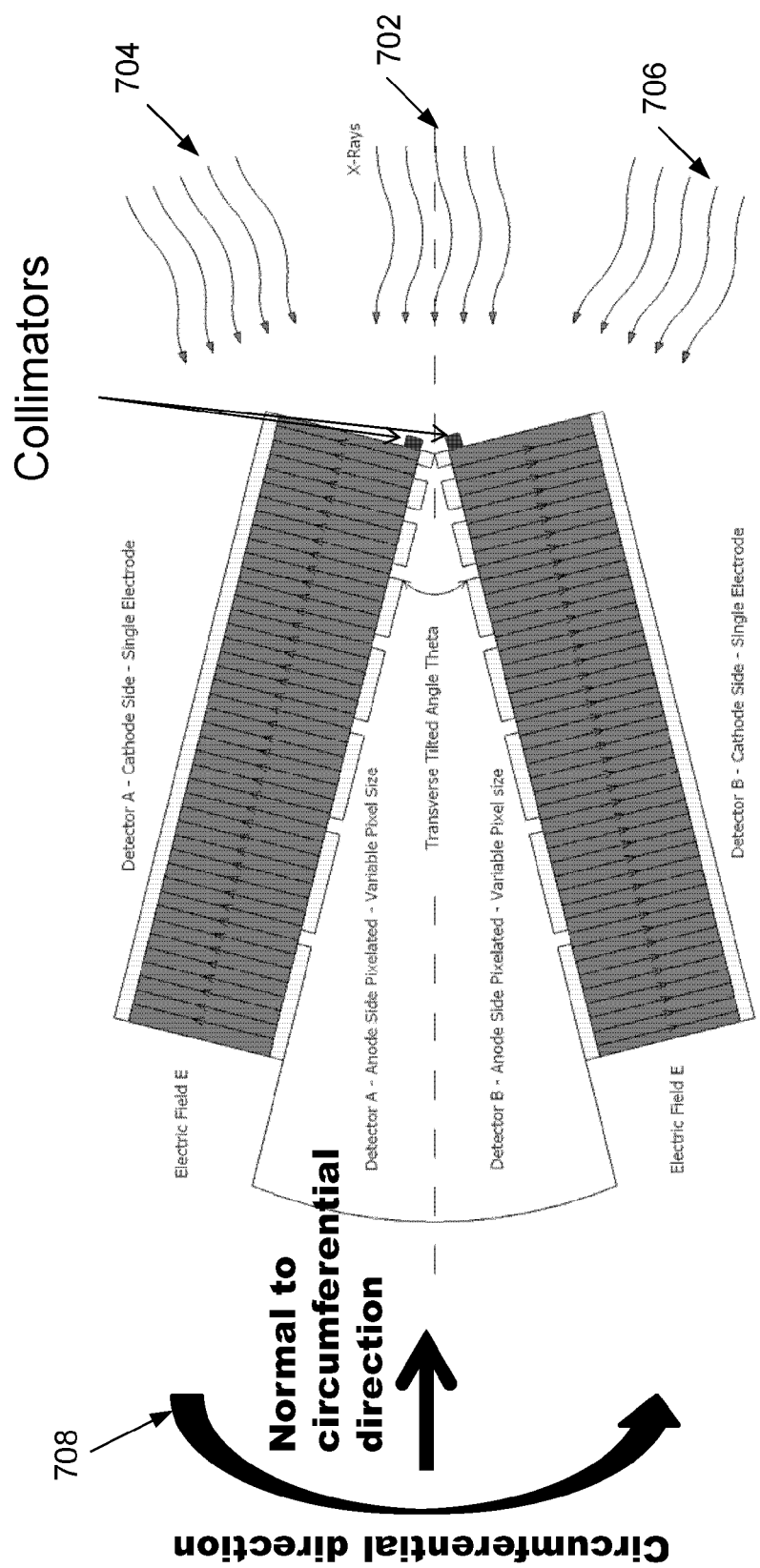
FIG. 7A illustrates an exemplary graph of a tilted and collimated PTF direct conversion photon-counting detector.
Figure 7B:
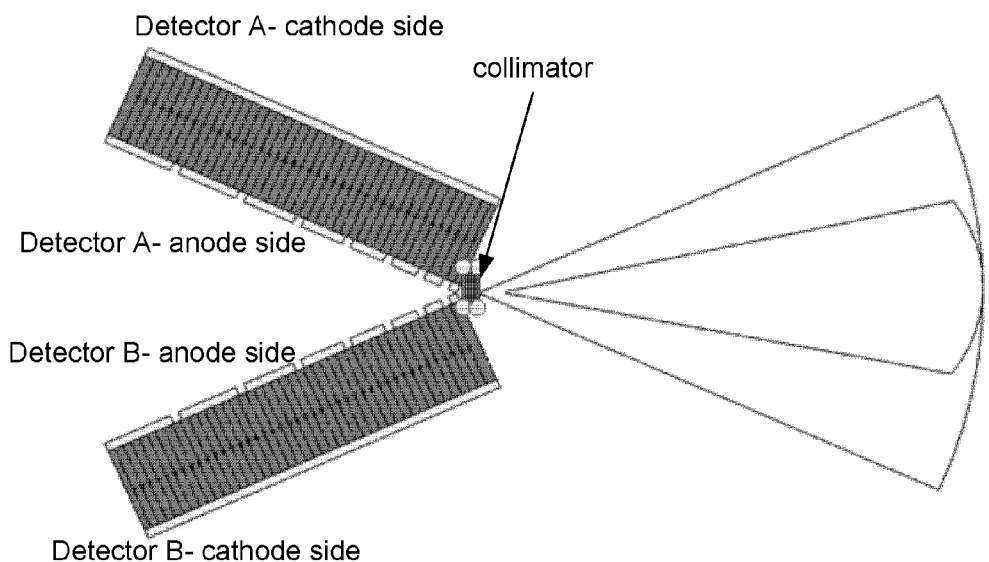
FIG. 7B illustrates an exemplary graph of a tilted and collimated PTF direct conversion photon-counting detector with an alternated tilted angle.

Now referring to FIG. 7A and FIG. 7B, a third embodiment of the PTF direct-conversion PCDs is illustrated. The third embodiment includes a pair of pixelated PTF direct-conversion PCDs and two collimators. This configuration of the PTF direct-conversion PCD is similar to the one described in FIG. 5. The two PTF direct-conversion PCDs (detectors A and B) are tilted with respect to the normal surface along the circumferential direction 708. As shown in FIG. 7A, the detector A is tilted clockwise along the circumferential direction with the pixelated anode side facing the normal face along the circumferential direction, and the detector B is tilted counter-clockwise along the circumferential direction with the pixelated-anode side facing the normal face along the circumferential direction. By tilting the detectors A and B, the X-rays 702, 704, and 706 enter the detectors in a symmetric manner. The transverse tilted angle θ is the angle between the anode sides of PCD A and the PCD B. Each PCD has a collimator, which is attached to the crystal close to the anode side, to block the incident X-rays between dotted lines where the interactions between the incident X-rays and the detectors provide very little energy information. The collimator dimensions are functions of the electrode design and can be further reduced to improve sensitivity.

FIG. 7B illustrates another embodiment having a different transverse tilted angle that is optimized for the optimal polar detector response. This embodiment enables high-count rates and a symmetric polar response for sparse fourth-generation PCDs.

Figure 8A:
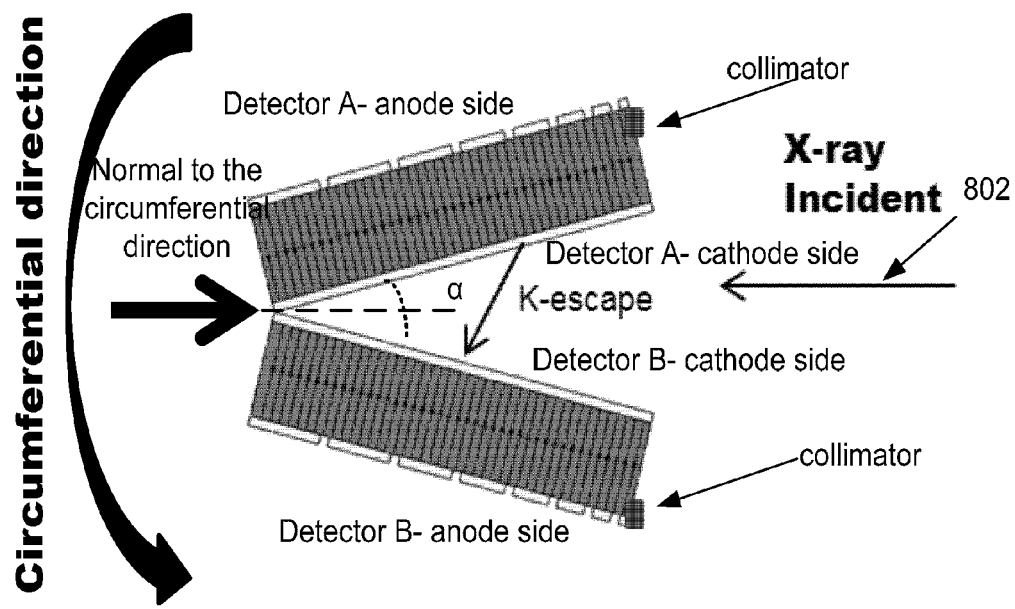
FIG. 8A illustrates an exemplary graph of a tilted and collimated PTF direct conversion photon-counting detector with an alternated cathode-to-anode position.

Now referring to FIG. 8A, another embodiment of the PTF direct-conversion PCDs is illustrated. This embodiment includes a pair of pixelated PTF direct-conversion PCDs and two collimators. This configuration of the PTF direct-conversion PCDs is similar to the one described in FIG. 5. The two PTF direct-conversion PCDs (detectors A and B) are tilted with respect to the normal surface to create a "well" to collect K-escape photons from the tilted PCDs A and B.

As shown in FIG. 8A, the detector A is tilted counter-clockwise, with the pixelated anode side facing the normal face to the circumferential direction, and the detector B is tilted clockwise, with the pixelated anode side facing the normal face to the circumferential direction. The X-ray 802 enters the well created by tilted detectors A and B. The transverse tilted angle α is the angle between the cathode sides of PCD A and the PCD B. The angle α can be set to optimize K-escape and incident spectral energy. Each PCD has a collimator, which is attached to the crystal close to the anode side, to block the incident X-ray where the interactions between the incident X-rays and detectors provide very little energy information. The collimator dimensions are functions of the electrode design and can be further reduced to improve sensitivity.

Figure 8B:
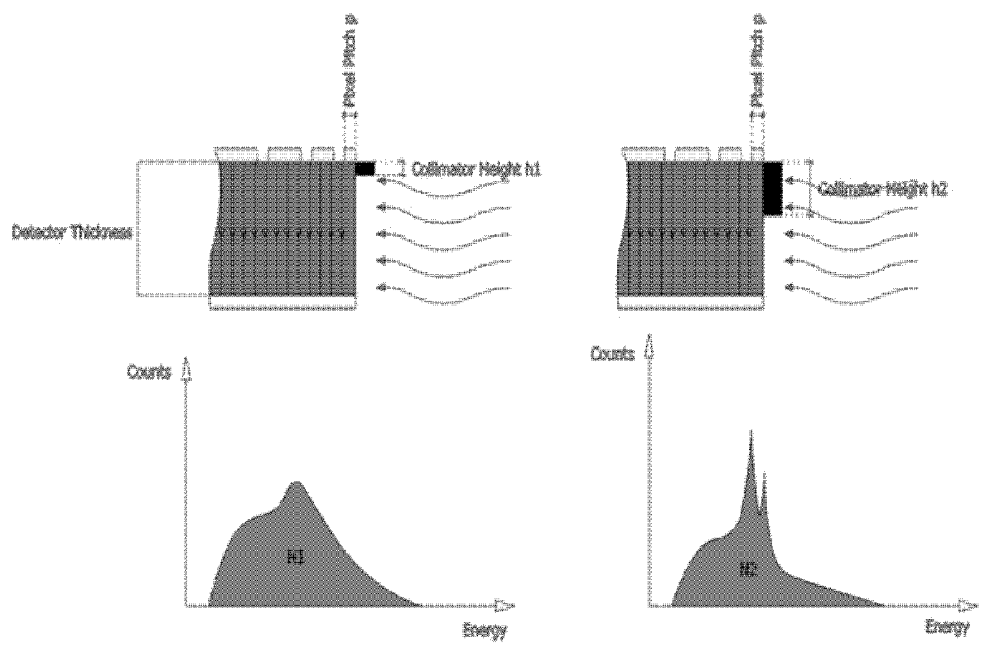
FIG. 8B illustrates an exemplary graph of a relationship between photon counts and the dimensions of the collimators.

FIG. 8B shows an example of changing the collimator dimension to improve the detector's sensitivity. The measured photon counts are proportional to the area of the detector that is not blocked by the collimator. By reducing the height of the collimator from h2 to h1, the counting efficiency is increased and the total counts are increased from N2 to N1. However, the spectral performance degrades when reducing the height of the collimator from h2 to h1.

Figure 9:
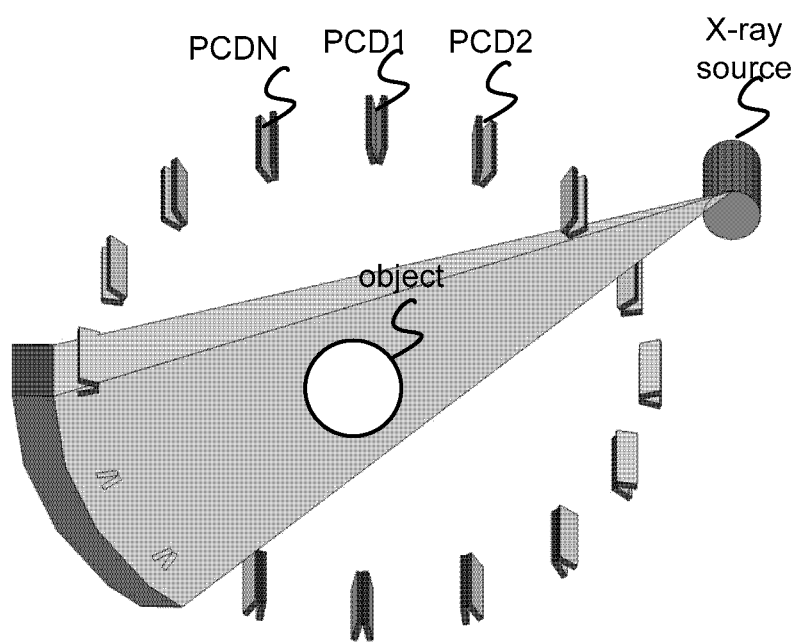
FIG. 9 illustrates an exemplary fourth-generation CT scanner with tilted and collimated PTF direct conversion photon-counting detectors.

FIG. 9 illustrates a fourth-generation CT scanner with tilted and collimated PTF direct-conversion photon-counting detectors. A predetermined number of tilted and collimated PTF direct conversion PCDs (e.g., PCD1 through PCDN) are sparsely placed around the object in a predetermined geometry, such as a circle. The X-ray source projects X-rays with a predetermined source fan beam angle around the object, while the X-ray source rotates around the object to be scanned.

Figure 10:
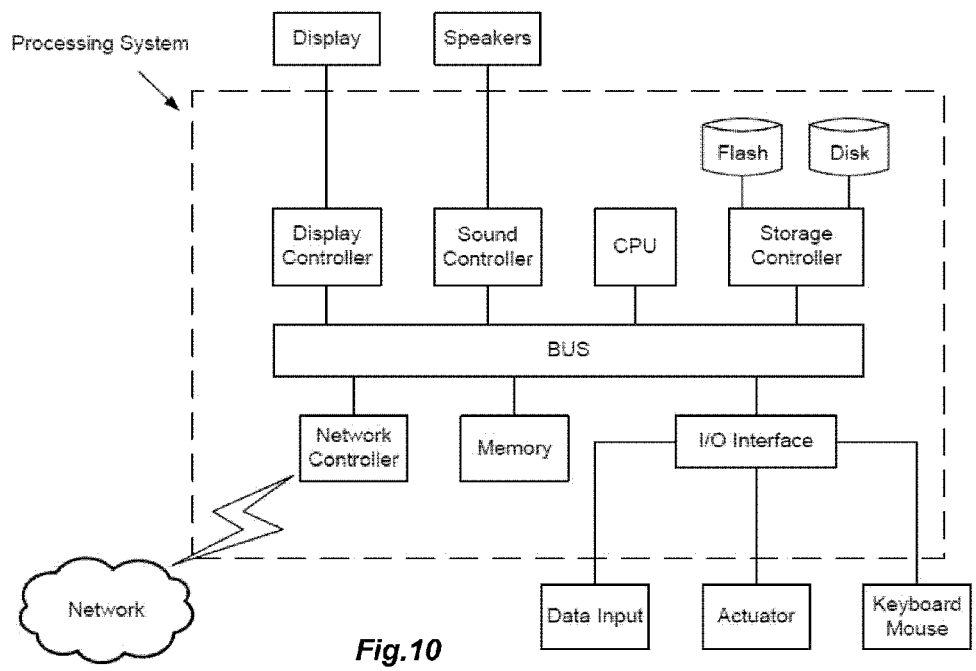
FIG. 10 shows a schematic diagram of an exemplary processing system.

An exemplary computer processing system is illustrated in FIG. 10, which can include the processor 6 shown in FIG. 1. The processor 6 can be a hardware device, e.g., a CPU that has been specifically configured to execute one or more computer programs that cause the CPU to perform the described function. In particular, this exemplary processing system can be implemented using one or more microprocessors or the equivalent, such as a central processing unit (CPU) and/or at least one application-specific processor ASP (not shown). A microprocessor is a circuit or circuitry that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure, and configured to execute the algorithms described herein. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing aspects of this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU and a graphics processing unit (GPU) to achieve improved computational efficiency. One or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central BUS is provided to connect the above hardware components together and provides at least one path for digital communication there between.

Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The data input portion of the processing system accepts input signals from a detector or an array of detectors by, e.g., respective wired connections. A plurality of ASICs or other data processing components can be provided as forming the Data Input portion, or as providing input(s) to the data input portion. The ASICs can receive signals from, respectively, discrete detector arrays or segments (discrete portions) thereof When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) detector apparatus, comprising:
a plurality of fixed photon-counting detector (PCD) modules arranged in a ring, each PCD module including a first Parallel-Transverse-Field (PTF) PCD that includes
a rectangular semiconductor crystal having a first face and a second face, wherein the first face and the second face are parallel;
a cathode side including a cathode electrode covering the first face;
an anode side including a plurality of anode pixels on the second face; and
a collimator covering only a portion of a side surface of the semiconductor crystal adjacent to the anode pixels, or covering a side surface of the semiconductor crystal that is adjacent to the anode pixels and covering the anode pixels, wherein the collimator blocks incident X-rays.

2. The apparatus of claim 1, wherein the PTF PCD is tilted with respect to a normal direction to a circumferential direction of the ring.

3. The apparatus of claim 2, wherein each PCD module includes a second PTF PCD that is tilted with respect to the normal direction to the circumferential direction of the ring.

4. The apparatus of claim 3, wherein each of the first and second PTF PCDs is tilted at a pre-determined angle with respect to the normal direction with the anode sides facing each other, the tilted PTF PCDs forming an opening facing away from a center of the ring.

5. The apparatus of claim 3, wherein each of the first and second PTF PCDs is tilted at a pre-determined angle with respect to the normal direction with the cathode sides facing each other, the tilted PTF PCDs forming an opening facing towards the center of the ring.

6. The apparatus of claim 1, wherein the semiconductor crystal is one of CdZnTe and CdTe.

7. A computed tomography (CT) apparatus, comprising:
an X-ray source configured to emit X-rays; and
a plurality of fixed photon-counting detector (PCD) modules arranged in a ring, each PCD module including a first Parallel-Transverse-Field (PTF) PCD that includes
a rectangular semiconductor crystal having a first face and a second face, wherein the first face and the second face are parallel;
a cathode side including a cathode electrode covering the first face;
an anode side including a plurality of anode pixels on the second face; and
a collimator covering only a portion of a side surface of the semiconductor crystal adjacent to the anode pixels, or covering a side surface of the semiconductor crystal that is adjacent to the anode pixels and covering the anode pixels, wherein the collimator blocks incident X-rays.

8. The apparatus of claim 7, wherein the PTF PCD is tilted with respect to a normal direction to a circumferential direction of the ring.

9. The apparatus of claim 8, wherein each PCD module includes a second PTF PCD that is tilted with respect to the normal direction to the circumferential direction of the ring.

10. The apparatus of claim 9, wherein each of the first and second PTF PCDs is tilted at a pre-determined angle with respect to the normal direction with the anode sides facing each other, the tilted PTF PCDs forming an opening facing away from a center of the ring.

11. The apparatus of claim 9, wherein each of the first and second PTF PCDs is tilted at a pre-determined angle with respect to the normal direction with the cathode sides facing each other, the tilted PTF PCDs forming an opening facing towards the center of the ring.

12. The apparatus of claim 7, wherein the semiconductor crystal is one of CdZnTe and CdTe.

* * * * *